US008921557B2

(12) United States Patent  (10) Patent No.: US 8,921,557 B2
Weber et al.  (45) Date of Patent: Dec. 30, 2014

(54) PREPARATION OF LOW IMPURITY OPIATES IN A CONTINUOUS FLOW REACTOR

(75) Inventors: Beat Weber, Zofingen (CH); Stefan Sahli, Zofingen (CH)

(73) Assignee: Siegfried AG, Zofingen (CH)

(*) Notice: Subject to any disclaimer, the term of this patent is extended or adjusted under 35 U.S.C. 154(b) by 0 days.

(21) Appl. No.: 13/582,334

(22) PCT Filed: Mar. 21, 2011

(86) PCT No.: PCT/EP2011/054193
§ 371 (c)(1),
(2), (4) Date: Oct. 19, 2012

(87) PCT Pub. No.: WO2011/117172
PCT Pub. Date: Sep. 29, 2011

(65) Prior Publication Data
US 2013/0035489 A1    Feb. 7, 2013

(30) Foreign Application Priority Data
Mar. 23, 2010  (EP) .................................... 10003023

(51) Int. Cl.
C07D 471/00  (2006.01)
C07D 491/00  (2006.01)
C07D 498/00  (2006.01)
C07D 513/00  (2006.01)
C07D 515/00  (2006.01)
C07D 489/00  (2006.01)
C07D 489/08  (2006.01)

(52) U.S. Cl.
CPC ................... C07D 489/08 (2013.01)
USPC ............................................ 546/45; 514/282

(58) Field of Classification Search
None
See application file for complete search history.

(56) References Cited

U.S. PATENT DOCUMENTS 6,090,943 A    7/2000  Mudryk et al.
7,071,336 B2   7/2006  Francis et al.
7,129,248 B2   10/2006 Chapman et al.
7,153,966 B2 * 12/2006 Casner et al. ................... 546/45
2006/0111383 A1  5/2006  Casner et al.

FOREIGN PATENT DOCUMENTS

WO  WO2006/019364       2/2006
WO  WO2006/094672       9/2006
WO  WO2008/048711       4/2008
WO  WO 2008/048711 A1 * 4/2008
WO  WO 2008/070658      6/2008
WO  WO2008/130553      10/2008
WO  WO2009/004491       1/2009
WO  WO2011/117172       9/2011

OTHER PUBLICATIONS

Jas, G. et al. Continuous Flow Techniques in Organic Synthesis. Chem. Eur. J. 2003, vol. 9, p. 5717, scheme 12 and p. 5721, Perspectives and Outlook, lines 12-14.*
Ley, SV. et al. The Use of a Continuous Flow-Reactor Employing a Mixed Hydrogen—Liquid Flow Stream for the Efficient Reduction of Imines to Amines. Chem Comm. 2005, vol. 00, p. 1.*
Heinzle, E. Introduction to Ideal Reactors. Technische Chemie I. 2009, table 2.*
Fletcher, NA. et al. Turn batch to continuous processing. Manufacturing Chemist. 2010, p. 24.*
Jas, G., and Kirschning, A., "Continuous Flow Techniques in Organic Synthesis," Chemistry—A European Journal. vol. 9 pp. 5708-5723 (2003).
Notification of Transmittal of the International Search Report and the Written Opinion of the International Searching Authority, or the Declaration corresponding to International Patent Applicaton No. PCT/EP2011/054193 dated dated Apr. 21, 2011.
Notification Concerning Transmittal of Copy of International Preliminary Report on Patentability (Chapter I of the Patent Cooperation Treaty) corresponding to International Patent Application No. PCT/EP2011/054193 dated Oct. 4, 2012.

* cited by examiner

*Primary Examiner* — Rita Desai
*Assistant Examiner* — Ben S Michelson
(74) *Attorney, Agent, or Firm* — Jenkins, Wilson, Taylor & Hunt, P.A.

(57) ABSTRACT

The present invention relates to a novel process for preparing opiates or salts thereof. More particularly, the present invention relates to oxidizing the starting material in a continuous flow reactor, followed by either an isolation of the intermediate, or a direct reduction reaction.

21 Claims, No Drawings

PREPARATION OF LOW IMPURITY OPIATES IN A CONTINUOUS FLOW REACTOR

FIELD OF THE INVENTION

The present invention relates to a process for preparing opiates having low levels of impurities. In particular, the process is useful for preparing opiates with low levels of α,β-unsaturated ketones.

BACKGROUND OF THE INVENTION

Oxycodone and oxymorphone are opioid analgesic medications synthesized from opium-derived thebaine or oripavine. 14-hydroxycodeinone and 14-hydroxymorphinone are the immediate precursors to oxycodone or oxymorphone in these syntheses. 14-hydroxycodeinone and 14-hydroxymorphinone belong to a class of compounds known as α,β-unsaturated ketones. These compounds have been designated as potential gene-toxins due to their susceptibility to the Michael addition reaction.

The following reaction scheme shows the conversion of thebaine to oxycodone via the intermediate 14-hydroxycodeinone.

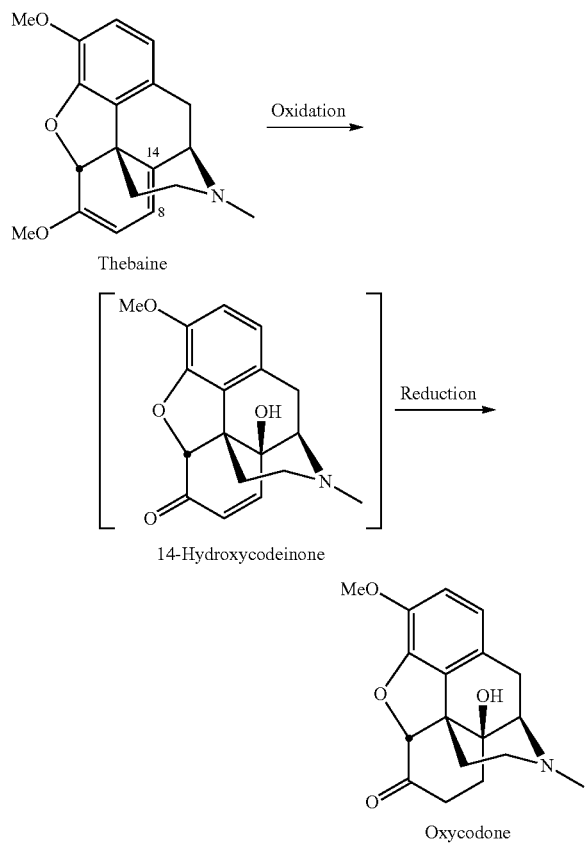

Oxymorphone can be produced by oxidation of oripavine, followed by reduction of the intermediate, as illustrated in the following scheme:

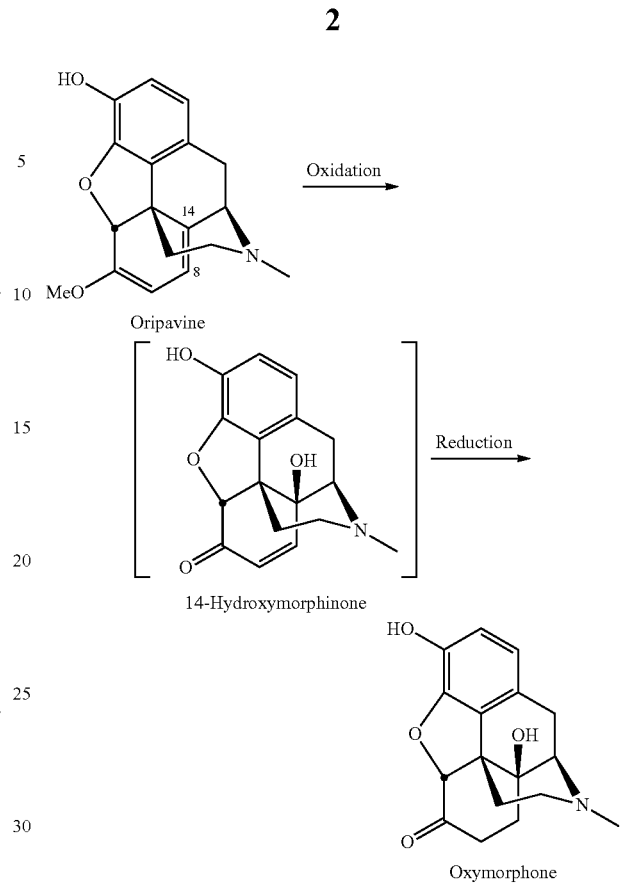

Oxycodone can be manufactured from thebaine by a process as disclosed for example in U.S. Pat. No. 6,090,943 B (Exp.8). Thebaine or a salt thereof is reacted with hydrogen peroxide in isopropanol, water and formic acid, producing 14-hydroxy-codeinone. The double bond in the 14-hydroxy-codeinone is reduced by reaction with hydrogen in the presence of a Pd/BaSO4 catalyst, providing oxycodone.

The International Patent Application WO 2008/130553 (Mallinckrodt Inc.) discloses an oxidation step of oripavine, said step comprising the in-situ formation of at least one peroxyacid. Moreover, the application discloses a reduction of the intermediate to form oxymorphone, utilizing catalytic hydrogen transfer reagent.

The International Patent Application WO 2008/048711 (Penick Corporation) describes a method of preparing oxymorphone from oripavine, including converting oripavine to 14-hydroxymorphinone and/or converting 14-hydroxymorphinone to oxymorphone.

U.S. Pat. No. 7,153,966 B (Johnson Matthey Public Limited) describes a method for the preparation of oxycodone from thebaine having low levels of impurities, such as 14-hydroxy-codeinone. According to said patent the pH must be adjusted before the hydrogenation step in order to achieve low levels of 14-hydroxycodeinone.

U.S. Pat. No. 7,071,336 B (Acura Pharmaceuticals) discloses a process for the preparation of oxycodone, which comprises the steps of oxidation of a composition including a thebaine component into 14-hydroxycodeinone, and reduction of 14-hydroxycodeinone to oxycodone, wherein the composition including the thebaine component comprises a concentrate of poppy straw.

U.S. Pat. No. 7,129,248 B (Euro-Celtique, S.A.) discloses a process for preparing an oxycodone hydrochloride composition having less than 25 ppm 14-hydroxycodeinone comprising hydrogenating an oxycodone hydrochloride composition having at least 100 ppm 14-hydroxycodeinone in a suitable solvent to produce an oxycodone composition having less than 25 ppm 14-hydroxycodeinone.

EP 1 658 293 B (Zentiva, A.S.) discloses a method of preparation of oxycodone by reaction of thebaine with hydrogen peroxide or peroxoacids in the presence of oxalic acid and of another organic acid. To the resulting crystalline precipitate of 14-hydroxy-codeinone oxalate is added a base to form 14-hydroxycodeinone, which is hydrogenated with hydrogen in the presence of a catalyst to yield oxycodone.

EP 1 861 405 B (Euro-Celtique S.A.) discloses a process for reducing the amount of α,β-unsaturated ketone in an opioid analgesic composition comprising hydrogenating a starting opioid analgesic composition having an α,β-unsaturated ketone impurity with diimide, a diimide progenitor, or a combination thereof in a suitable solvent.

The International Patent Application WO 2008/070658 (Noramco Inc.) discloses a process for preparing oxycodone and oxycodone HCl with low levels of 14-hydroxycodeinone, comprising heating the mixture of oxycodone (HCl) and a sulfite compound in an alcohol/water solvent under basic conditions and isolating said oxycodone (HCl).

The International Patent Application WO 2009/004491 (Alpharma APS) discloses a one-pot process for the preparation of oxycodone from thebaine which comprises (i) oxidation of thebaine to 14-hydroxycodeinone with a peroxide; and (ii) reduction of 14-hydroxycodeinone with hydrogen, characterised in that: (iii) the oxidation reaction is carried out on more than 50 g of thebaine, and (iv) both the oxidation and reduction reactions are carried out in acetic acid or propionic acid; and (v) both the oxidation and reduction reactions are carried out in the same vessel without isolation of the 14-hydroxycodeinone; and (vi) the oxidation reaction is performed at a temperature below 35° C.

However, all the cited processes are complicated and time consuming. Therefore, there is still a need to improve the process for preparing opiates having low levels of impurities.

SUMMARY OF THE INVENTION

The object of the present invention is to provide a safe, ecological and economical process for preparing opiates in high yield having low levels of impurities, specially low levels of α,β-unsaturated ketones.

This object is solved by the subject-matter of the independent claims. Preferred embodiments are indicated in the dependent claims.

The present invention provides a process for preparing opiates, which comprises a method for converting a compound according to Formula I or a salt thereof to a compound according to Formula II or a salt thereof, and further converting a compound according to Formula II or a salt thereof to Formula III or a salt thereof, said process comprising (a) oxidizing the compound according to Formula I or a salt thereof in a continuous flow reactor to form the compound according to Formula II or a salt thereof

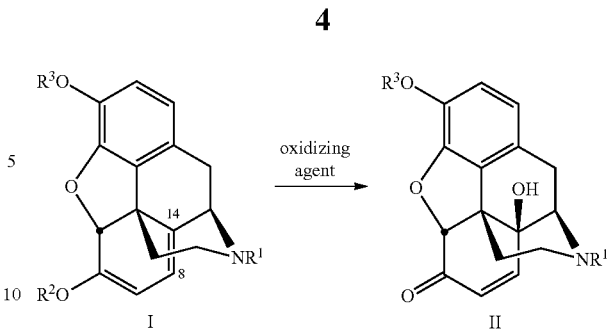

wherein R1, is selected from H; CH3; C2-C6 alkyl, optionally unsaturated and/or branched; and C1-C4 alkyl, substituted with cycloalkyl group(s); and R2 and R3 are selected from H and CH3; and (b) isolating the Formula II or a salt thereof, followed by a reduction reaction to form Formula III or a salt thereof; or (c) reducing the compound according to Formula II or a salt thereof, without isolation, to form the compound according to Formula III or a salt thereof wherein R1 is selected from H; CH3; C2-C6 alkyl, optionally unsaturated and/or branched; and C1-C4 alkyl, substituted with cycloalkyl group(s) and R3 is selected from H and CH3.

It has been surprisingly found that opiates having less than 50 ppm α,β-unsatured ketones can be obtained by performing the oxidation reaction in a continuous flow reactor. The directly following reduction step or the directly performed isolation of the intermediate, suppresses the formation of critical side products. Further, the oxidation can be conducted at higher concentrations without causing safety risks due to the continuous process.

In general, the continuous flow reactor allows easy and accurate handling and good control over reaction conditions including pressure, heat transfer, time and mixing.

DETAILED DESCRIPTION OF THE INVENTION

Hereinafter, the best mode for carrying out the present invention is described in detail.

The present invention provides an improved method for the conversion of the compound according to Formula I or a salt thereof to a compound according to Formula II or a salt thereof, and further converting the compound according to Formula II or a salt thereof to a compound according to Formula III or a salt thereof. The conversion of a compound according to Formula I or a salt thereof to a compound according to Formula II or a salt thereof comprises an oxidation step in a continuous flow reactor.

The compound according to Formula II or a salt thereof is further, either first isolated and then reduced to a compound according to Formula III or a salt thereof, or reduced directly to a compound according to Formula III or a salt thereof

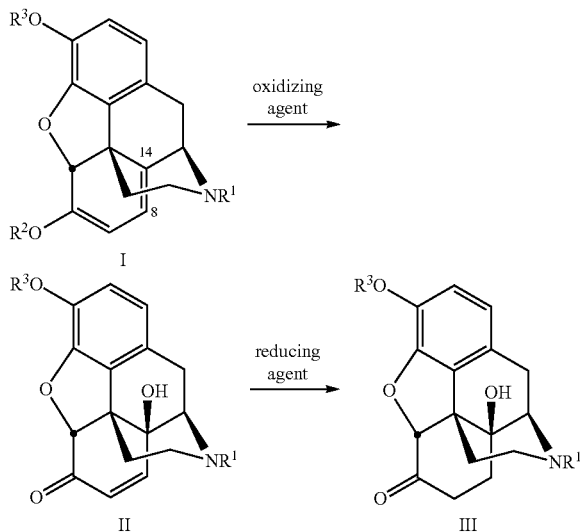

wherein R1 is selected from H; CH3; C2-C6 alkyl, optionally unsaturated and/or branched; and C1-C4 alkyl, substituted with cycloalkyl group(s) and R2 and R3 are selected from H and CH3.

The oxidation step is conducted in a continuous flow reactor. Said step comprises dissolving Formula I in a solvent, wherein an oxidant is premixed. Subsequent, the mixture is pumped continuously through a continuous flow reactor. In another embodiment, Formula I in a solvent as well as the oxidant are subjected by two independent pumps to the continuous flow reactor.

The oxidant can comprise any oxidizing agent that permits the conversion of Formula I to Formula II, including hydrogen peroxide and peroxy acids, such as performic acid, peracetic acid, and m-chloroperoxybenzoic acid (MCPBA). Mixtures of oxidizing agents may be used. When a peroxy acid is used, it may be added, or prepared in situ.

The oxidation reaction may be carried out in any appropriate solvent. In a preferred embodiment, the solvent is an organic acid, more preferably selected from formic acid, acetic acid or a mixture thereof.

The solvent may further comprise an inorganic acid.

The continuous oxidation reaction is carried out at any temperature that permits the reaction to be performed, preferably at the temperature in the range of −30-160° C., more preferably in the range of 5-130° C., and most preferably in the range of 20-110° C.

The residence time is any period of time that permits the oxidation reaction to be performed in a continuous flow reactor, preferably the residence time is up to 30 min.

The remaining amount of Formula I in the reaction mixture can be determined by any method, preferably by HPLC.

In one embodiment, wherein the intermediate (Formula II or a salt thereof) is isolated after the oxidation reaction, the product flow is transferred from the continuous flow reactor directly to a solvent containing an inorganic acid, whereupon the corresponding salt of Formula II is precipitated and isolated.

Any appropriate solvent may be used. In a preferred embodiment, the solvent is selected from 2-propanol or acetone.

Any appropriate inorganic acid may be used. Preferably, the acid is selected from methanesulphonic acid, sulphuric acid, phosphoric acid and hydrochloric acid. The most preferably acid is hydrochloric acid.

The isolated Formula II, or a salt thereof, is further reduced to Formula III or a salt thereof. The isolated intermediate is first dissolved in an alcoholic solvent, optionally comprising an acid. In a preferred embodiment, the reduction step is a hydrogenation reaction.

Any appropriate alcoholic solvent may be used. In a preferred embodiment, the alcohol is selected from C1-C4 alcohols. More preferably the alcohol is selected from methanol, ethanol and propanol.

Any appropriate acid may be used. Preferably the acid is selected from the group of formic acid, acetic acid, methanesulphonic acid, sulphuric acid, phosphoric acid and hydrochloric acid. The most preferred acid is formic acid.

In another embodiment, wherein the reduction reaction follows without isolating the intermediate (Formula II or a salt thereof), the product flow is transferred from the continuous flow reactor directly to an autoclave, which is preferably charged with an alcoholic solvent. Optionally, an acid is added to the reaction mixture. In a preferred embodiment, the reduction step is a hydrogenation reaction.

Any appropriate alcoholic solvent may be used. In a preferred embodiment, the alcohol is selected from C1-C4 alcohols. More preferably the alcohol is selected from methanol, ethanol and propanol. The most preferred alcohol is 2-propanol.

Any appropriate acid may be used. Preferably the acid is selected from the group of formic acid, acetic acid, methanesulphonic acid, sulphuric acid, phosphoric acid and hydrochloric acid. The most preferred acid is formic acid.

The following reaction conditions of the hydrogenation reaction apply for the reduction reaction of the isolated intermediate as well as for the direct reduction reaction.

The hydrogenation reaction is preferably effected by adding a catalyst and holding the reaction mixture under hydrogen gas (H2). The hydrogen gas is applied at a pressure known to the man skilled in the art.

In a preferred embodiment, the catalyst is a palladium catalyst. Preferably, the palladium catalyst is a carbon supported palladium catalyst, well known in the art.

The hydrogenation reaction is carried out at any temperature that permits the reaction to be performed, preferably at a temperature in a range of 50-125° C., and more preferably in the range of 80-100° C.

The hydrogenation reaction is carried out in an autoclave equipped with stirring means. The reaction mixture is preferably stirred at least 2 hours. More preferably, the stirring time is 2-24 hours.

The following process-scheme shows a method for preparing opiates by using a continuous flow reactor followed by a hydrogenation reaction:

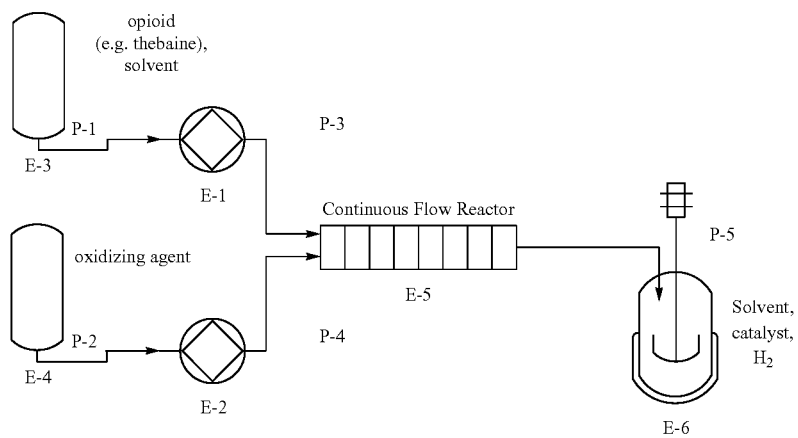

After the hydrogenation, the catalyst is filtered off and the crude mixture is basified to a pH>8.5, preferably with sodium hydroxide, to obtain Formula III base precipitate. The precipitate is filtered off and preferably washed with water or with water mixed with an aliphatic alcohol to obtain low impurity Formula III base.

Any salt of Formula III, preferably a pharmaceutically acceptable salt, may be prepared. In a preferred embodiment, a hydrochloride salt of Formula III may be prepared by adding to the filtrate 2-propanol or acetone, and acidifying said mixture with hydrochloric acid. The Formula III HCl precipitate is filtered off and washed with 2-propanol or acetone to yield low impurity Formula III HCl.

Formula III, or salts thereof, may further be prepared into pharmaceutical dosage forms using methods known to the man skilled in the art.

Hereinafter, the present invention is illustrated in more detail by the examples, which however are not intended to limit the present invention.

Example 1

Preparation of Oxycodone

Thebaine (67 g, 0.215 mol) was dissolved in formic acid (98-100%, 120 g) and hydrogen peroxide (30% in water, 24.5 g, 0.216 mol) added at 0° C. The mixture was pumped continuously at 2 ml/min through a 30 ml continuous flow reactor at 80° C. (15 min residence time). An analytical control after the continuous reactor showed less than 1% Thebaine remaining. The continuous stream was added directly to the hydrogenation autoclave that was precharged with 2-propanol (204 g), formic acid (98-100%, 64 g) and 5% Pd/C (7.6 g) and held at 100° C. under $H_2$ (40 bar). The hydrogenation was stirred for 16 h. After the hydrogenation, the catalyst was filtered off and the crude mixture was either basified with NaOH to obtain the low impurity Oxycodone base, or treated with HCl in 2-Propanol to give the Oxycodone HCl. The yields were 82% for the base and 78% for the HCl salt. The 14-Hydroxycodeinone content of the base was 49 ppm and of the HCl salt 29 ppm.

Example 2

Preparation of Oxycodone

Solution 1:
Thebaine (100 g, 0.321 mol) was dissolved in formic acid (100 g) and acetic acid (100 g); volume 253 ml. Solution 2: Peracetic acid (39% in acetic acid, 63.25 g, 0.325 mol) was diluted with acetic acid to give a solution of 85 ml volume. The two solutions were pumped through the continuous flow reactor in the ratio 6 ml/min solution 1 to 2 ml/min solution 2 at 20° C. (4 min residence time). An analytical control after the continuous reactor showed less than 4% Thebaine remaining. The continuous stream was added directly to the hydrogenation autoclave that was precharged with 2-propanol (60 g), formic acid (98-100%, 10 g) and 5% Pd/C (2.5 g) and held at 100° C. under $H_2$ (40 bar). The hydrogenation was stirred for 16 h. After the hydrogenation, the catalyst was filtered off and the crude mixture was either basified with NaOH to obtain the low impurity Oxycodone base, or treated with HCl in 2-Propanol to give the Oxycodone HCl. The yields were 74% for the base and 73% for the HCl salt. The 14-hydroxycodeinone content of the base was 27 ppm and of the HCl salt <10 ppm.

Example 3

Preparation of Oxycodone

Thebaine (67 g, 0.215 mol) was dissolved in formic acid (98-100%, 120 g) and hydrogen peroxide (30% in water, 24.5 g, 0.216 mol) added at 0° C. The mixture was pumped continuously at 2 ml/min through a 30 ml continuous flow reactor at 80° C. (15 min residence time). An analytical control after the continuous reactor showed less than 1% Thebaine remaining. The continuous stream was added directly to acetone, containing 32% HCl, whereupon the 14-Hydroxycodeinone HCl was precipitated and isolated in 80% yield. The 14-Hydroxycodeinone HCl was then dissolved in MeOH and HCOOH (4:1 w/w) and hydrogenated at 80° C. under 15 bar $H_2$ pressure. The hydrogenation was stirred for 20 h. After the hydrogenation, the catalyst was filtered off and the crude mixture was either basified with NaOH to obtain the low impurity Oxycodone base, or treated with HCl in 2-Propanol to give the Oxycodone HCl. The 14-Hydroxycodeinone content of the base was 48 ppm.

Example 4

Preparation of Oxymorphone

Oripavine (64 g, 0.215 mol) was dissolved in formic acid (98-100%, 120 g) and hydrogen peroxide (30% in water, 24.5 g, 0.216 mol) added at 0° C. The mixture was pumped continuously at 2 ml/min through a 30 ml continuous flow reactor at 80° C. (15 min residence time). An analytical control after the continuous reactor showed less than 1% Oripavine remaining. The continuous stream was added directly to the hydrogenation autoclave that was precharged with 2-propanol (204 g), formic acid (98-100%, 64 g) and 5% Pd/C (7.6 g) and held at 100° C. under H₂ (40 bar). The hydrogenation was stirred for 16 h. After the hydrogenation, the catalyst was filtered off and the crude mixture was either basified with NaOH to obtain the low impurity Oxymorphone base, or treated with HCl in 2-Propanol to give the Oxymorphone HCl. The yield was 82% for the base.

The invention claimed is:

1. A process for converting a compound according to Formula I or a salt thereof to a compound according to Formula III or a salt thereof, the process comprising:
   (a) oxidizing the compound according to Formula I or a salt thereof in a continuous flow reactor for up to 30 minutes at a temperature in the range of 80-160° C. to form the compound according to Formula II or a salt thereof

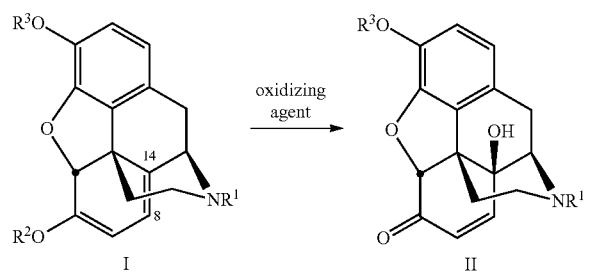

wherein $R^1$ is selected from H; $CH_3$; $C_2$-$C_6$ alkyl, optionally unsaturated and/or branched; and $C_1$-$C_4$ alkyl, substituted with cycloalkyl group(s) and $R^2$ and $R^3$ are selected from H and $CH_3$; and
   (b) isolating the compound according to Formula II or a salt thereof, followed by a reduction reaction to form a compound according to Formula III or a salt thereof; or
   (c) reducing the compound according to Formula II or a salt thereof, without isolation, to form a compound according to Formula III or a salt thereof

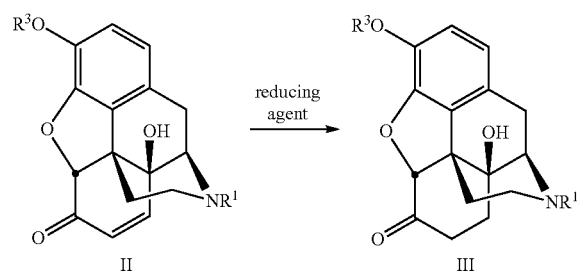

wherein $R^1$ is selected from H; $CH_3$; $C_2$-$C_6$ alkyl, optionally unsaturated and/or branched; and $C_1$-$C_4$ alkyl, substituted with cycloalkyl group(s) and $R^3$ is selected from H and $CH_3$.

2. A process according to claim 1, wherein the oxidation (a) is carried out in the presence of an oxidation agent.

3. A process according to claim 1, wherein the oxidation step (a) is carried out in the presence of a solvent.

4. A process according to claim 3, wherein the oxidation step (a) is further carried out in the presence of an acid.

5. A process according to claim 1, wherein the isolation step (b) is carried out in a solvent comprising an inorganic acid.

6. A process according to claim 1, wherein the reduction reaction according to (b) or (c) is a hydrogenation reaction, which is carried out in the presence of an alcoholic solvent.

7. A process according to claim 6, wherein the hydrogenation is further carried out in the presence of an acid.

8. A process according to claim 6, wherein the hydrogenation is carried out at a temperature in the range of 50-125° C.

9. A process according to claim 6, wherein the hydrogenation is carried out over a period of time of at least 2 hours.

10. A process for preparing opiates, wherein the process comprises using a continuous flow reactor in an oxidation step, wherein using the continuous flow reactor comprises oxidizing a compound according to Formula I or a salt thereof with an oxidant in the continuous flow reactor for up to 30 minutes at a temperature in the range of 80-160° C. to form a compound according to Formula II or a salt thereof

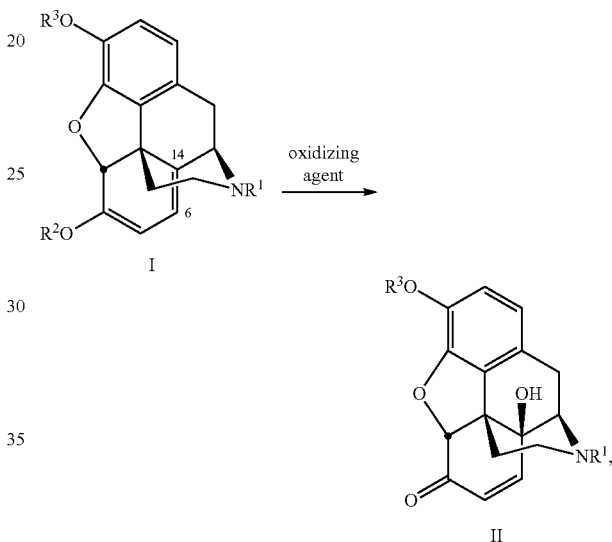

wherein $R^1$ is selected from H; $CH_3$; $C_2$-$C_6$ alkyl, optionally unsaturated and/or branched; and $C_1$-$C_4$ alkyl, substituted with cycloalkyl group(s) and $R^2$ and $R^3$ are selected from H and $CH_3$.

11. A process according to claim 2, wherein the oxidation agent is selected from hydrogen peroxide, peroxy acids or a mixture of hydrogen peroxide and organic acid(s).

12. A process according to claim 3, wherein the solvent is an acid.

13. A process according to claim 12, wherein the acid is an organic acid.

14. A process according to claim 1, wherein the oxidation (a) is carried out at a temperature in the range of 80-130° C.

15. A process according to claim 14, wherein the oxidation (a) is carried out at a temperature in the range of 80-110° C.

16. A process according to claim 6, wherein the alcoholic solvent is $C_1$-$C_4$ alcohol.

17. A process according to claim 7, wherein the acid is an organic acid.

18. A process according to claim 17, wherein the organic acid is formic acid.

19. A process according to claim 8, wherein the hydrogenation is carried out at a temperature in the range of 80-100° C.

20. A process according to claim 9, wherein the hydrogenation is carried out over a period of time of in the range of 2-24 hours.

21. A process according to claim 12, wherein the oxidation step (a) is carried out in the presence of a further acid.

* * * * *